US006077293A

United States Patent [19]
King

[11] Patent Number: 6,077,293
[45] Date of Patent: Jun. 20, 2000

[54] CHIROPRACTIC TABLE

[76] Inventor: Wallace E. King, 2401 S. Washington St., Grand Forks, N. Dak. 58201

[21] Appl. No.: 09/270,138

[22] Filed: Mar. 16, 1999

Related U.S. Application Data

[60] Provisional application No. 60/117,922, Jan. 28, 1999.

[51] Int. Cl.$^{7}$ .......... A61F 5/00
[52] U.S. Cl. .......... 606/237; 601/98
[58] Field of Search .......... 606/240, 237; 601/24, 97, 98

[56] References Cited

U.S. PATENT DOCUMENTS 5,876,358 3/1999 Goebel .......... 601/98

*Primary Examiner*—Michael Buiz
*Assistant Examiner*—Julian W. Woo
*Attorney, Agent, or Firm*—Robert E. Kleve

[57] ABSTRACT

The invention comprises a chiropractic table having a main table with a pair of slots in the upper surface of the table and a chiropractic back engaging spinal treatment mechanism is mounted in one slot and a lower posterior engaging sacral iliac treatment mechanism is mounted in the other slot. The back spinal treatment mechanism comprises a pair of back engaging ridge members in the slot with the upper edges of the ridges projecting above the upper surface of the table for the back of a patient to rest upon on opposite sides of its spine. The ridge members are movable downward and bilaterally away from one another in reaction to frontal pressure upon the patient with stop members at the outer end of their movement with springs urging the ridge members back toward one another whereby a treatment operator may press down on the chest/arms of the patient and the impact reaction upon the ridge members will produce the ridge members to separate apart while engaging the patient's back on each opposite sides of the spinal column to cause realignment of spinal sublucated components of the patient. The lower posterior sacrum engaging mechanism for the sacrum of the patient to rest upon comprises a pair of posterior engaging ridge mechanisms for engaging the sacrum posterior of the patient and reactive to downward pressure upon the patient to spread bilaterally apart to engage medial posterior superior iliac spine of the patient's sacral iliac joint tor realigning the same.

5 Claims, 8 Drawing Sheets

CHIROPRACTIC TABLE

This application claims benefit of Provisional Application Ser. No. 60/117,922 filed Jan. 28, 1999.

This invention relates to chiropractic tables.

It is an object of the invention to provide a novel chiropractic table having a back engaging upper spinal treatment mechanism and a second lower posterior engaging mechanism mounted in slots in the top of the table for engaging the back and posterior of a patient, respectively, while treating a patient for spinal and sacral iliac problems of the patient where the patient is on his back supine upon the table.

It is a further object of the invention to provide a novel back engaging mechanism mounted on a table for engaging the back of a patient laying supine on the table which has a pair of separable ridge members to engage the back on each side of the spine and under downward pressure by a treatment operator will react and separate apart in a manner to facilitate the realignment of dislocated portions of the spine, and which has a spring return to bring the ridge members back toward one another upon release of the downward pressure by the treatment operator.

It is another object of the invention to provide a novel chiropractic treatment table having a separable pair of back ridge like mounds which project slightly above the adjacent top surface of the table and act to engage the back of patient, when lying supine on the table, on opposite sides of the spine of the patient and with downward pressure upon the patient's chest acting to cause the mounds to separate in bilateral parallel action away from one another under a spring return action facilitating the realignment of displaced portions of the spine of the patient.

It is another object of the invention to provide novel parallel projecting ridges mechanism on a treatment table which ridges may move apart and downward and terminate in abrupt stop, due to downward impact pressure upon the front of a patient resting his back or lower posterior upon the ridges, and while under spring resistance; and which movement apart tends to trigger slight momentary separation to articulation of joint components of the body when out of alignment so as to be allowed them to move back into component alignment, and with the ridge movement terminating in an abrupt drop or stop to force the components back into alignment upon their separation due the initial ridge movement.

It is another object of the invention to provide a novel spinal treatment table which provides a lateral opposing separation movement or action and an abrupt drop or stop at the end of the separation movement to separate and then force joint components of a patient into proper alignment.

It is another object of the invention to provide a novel chiropractic treatment table having mechanisms for treating upper spinal and lower sacral-iliac problems of a patient.

It is another object of the invention to provide a novel chiropractic treatment table having mechanism for treating patients with chiropractic mechanical problems.

Further objects and advantages of the invention will become apparent as the description proceeds and when taken in conjunction with the accompanying drawings wherein:

BRIEF DESCRIPTION OF PREFERRED EMBODIMENT

Briefly stated, the invention comprises a chiropractic table having a main table member with a pair of slots in the upper surface of the table. A pair of back engaging spinal treatment ridge members are positioned in one of the slots of the table and are movably mounted in the slot to move in bilateral parallel travel away and downward from one another in said slot, with the upper surface of the pair of ridge members projecting slightly above the upper surface of the table member for engagement with the back of a patient lying supine on the table on opposite sides of the patient's spine, whereby downward pressure upon the chest of the patient reactively triggers the ridge members to move bilaterally apart while engaging the back for spinal articulation treatment, with spring return means mounted between the ridge members to urge them toward one another upon completion of the bilateral parallel travel. A second pair of sacral iliac treatment ridges members similar to the first in the table for the patient's sacrum to rest upon are movably mounted in the second slot for bilateral separation and downward movement from one another in reaction to downward pressure upon the lower front of the patient supine upon the table while his lower back unit is supported on the ridge members for treating sacral-iliac problems of a patient.

Preferred Form of the Invention

Figure 1:
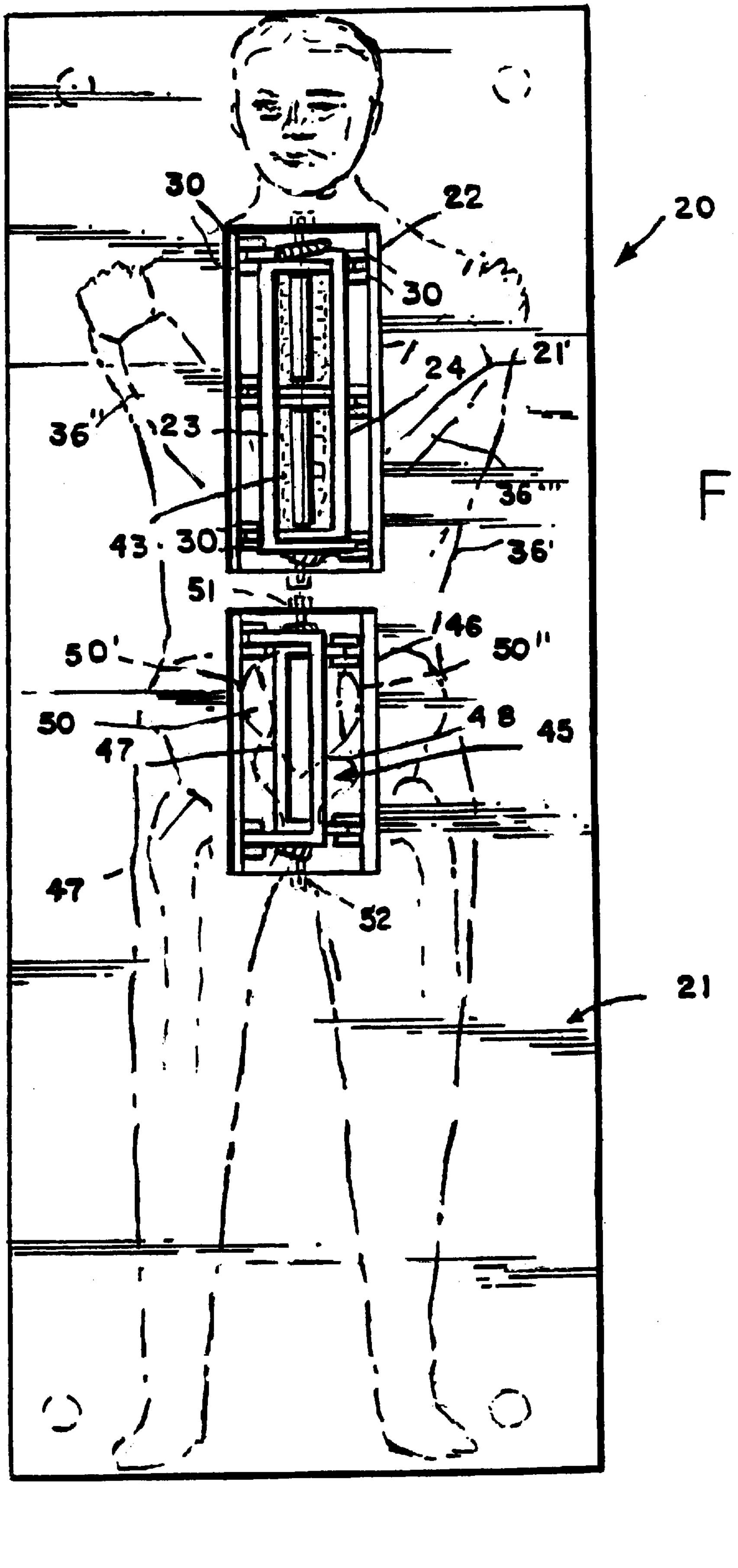
FIG. 1 is a top plan view of the preferred form of treatment table showing a back posterior engaging mechanism or upper unit in an upper slot along the top surface of the table and a lower posterior engaging mechanism or lower unit in a lower slot along the top surface with each mechanism having a pair of elongated ridge members mounted in their respective slot in the table and projecting upward projecting in spaced relation with one pair of ridge members for engaging the upper back on each parallel side of the spine of a patient and the other pair of ridge members for engaging the lower posterior sacrum of the patient, respectively, and each pivotally movable apart for moving the spinal components and sacral iliac joints, respectively, in a scissor like separation action.
Figures 2, 3, 4:
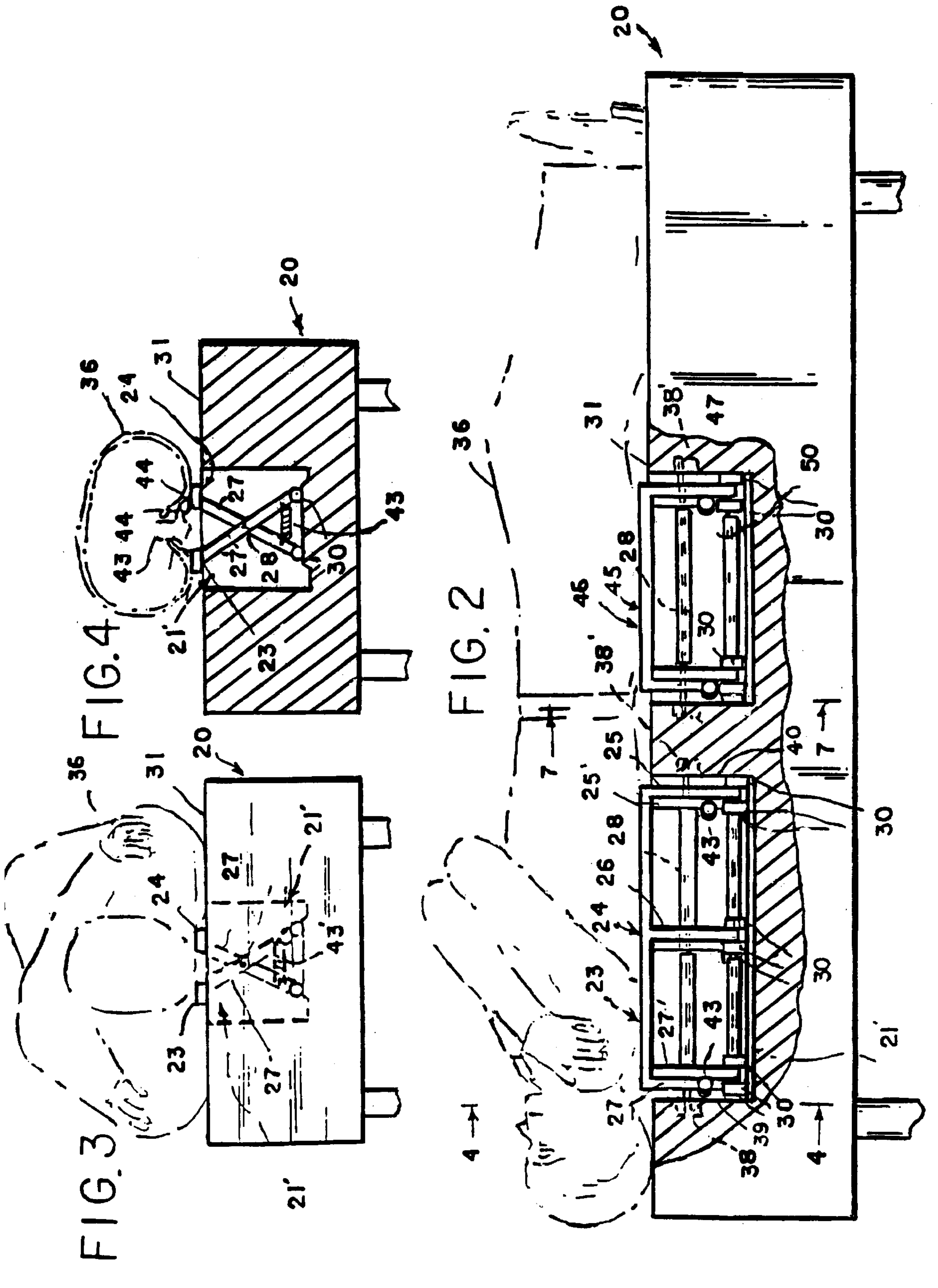
FIG. 2 is a side elevational view of the preferred form of treatment table illustrating the upper and lower units of the preferred form of the invention, with portions of the pair of slots cutaway to reveal the dual pair of the ridge members mounted pivotally connected together and movable apart in a scissor like action for the spinal and sacral iliac joint treatment, respectively.
FIG. 3 is a front elevational view of the preferred from of treatment table with a patient lying on his back on the table.
FIG. 4 is a similar view to FIG. 3 with a side cutaway of table and an a illustration of the chest and spine of a patient when lying on the table in relation to the pair of pivotally movable ridge members taken along line 4—4 of FIG. 2.

Referring more particularly to the drawings, in FIGS. 1, the preferred embodiment of the chiropractic table invention 20 is illustrated in FIGS. 1–8, inclusive, having a treatment table 21 and a movable back engaging spinal treatment ridge apparatus 21' having a pair of back engaging ridges 23 and 24 for engaging the back of a patient 36' on opposite sides of the patient's spine 43 for spinal treatment is mounted in the slot 22 of the table 21 of the invention. A second sacral iliac treatment mechanism 45 mounted in a second slot 46 in the table has a pair of ridges 47 and 48 for resting upon and engaging the sacrum 50 of the patient at the lower posterior of a patient for treatment of sacral iliac joints. The movable back ridge apparatus 21' or upper unit has a pair of elongated movable ridges 23 and 24 which are mounted on three pair of scissor like supports 25, 25', 26,26' and 27,27'. Each pair of ridges moves bilaterally apart from one another to engage the iliac spine of the patient in a pivoting scissor like movement by means of the three pair of scissor like supports 25,25',26,26',27,27'. Each pair of scissors are pivotally connected together intermediate their length by a common rod 28 wluch extends though all three pair of scissors. One pair of scissors 25,25' are mounted at their one ends to one of the ends of the parallel ridges one pair of scissors 27,27' are mounted at their one ends to the other ends of the parallel ridges, and the third pair of parallel ridges are mounted at their one ends to the middle of the parallel ridges 23 and 24. The other ends 29 of the scissors have rollers 30 rotatably mounted thereon with the rollers adapted to roll on the horizontal surface portion 31 of the bottom panel 32 in the slot 22 of the treatment table.

Figure 5:
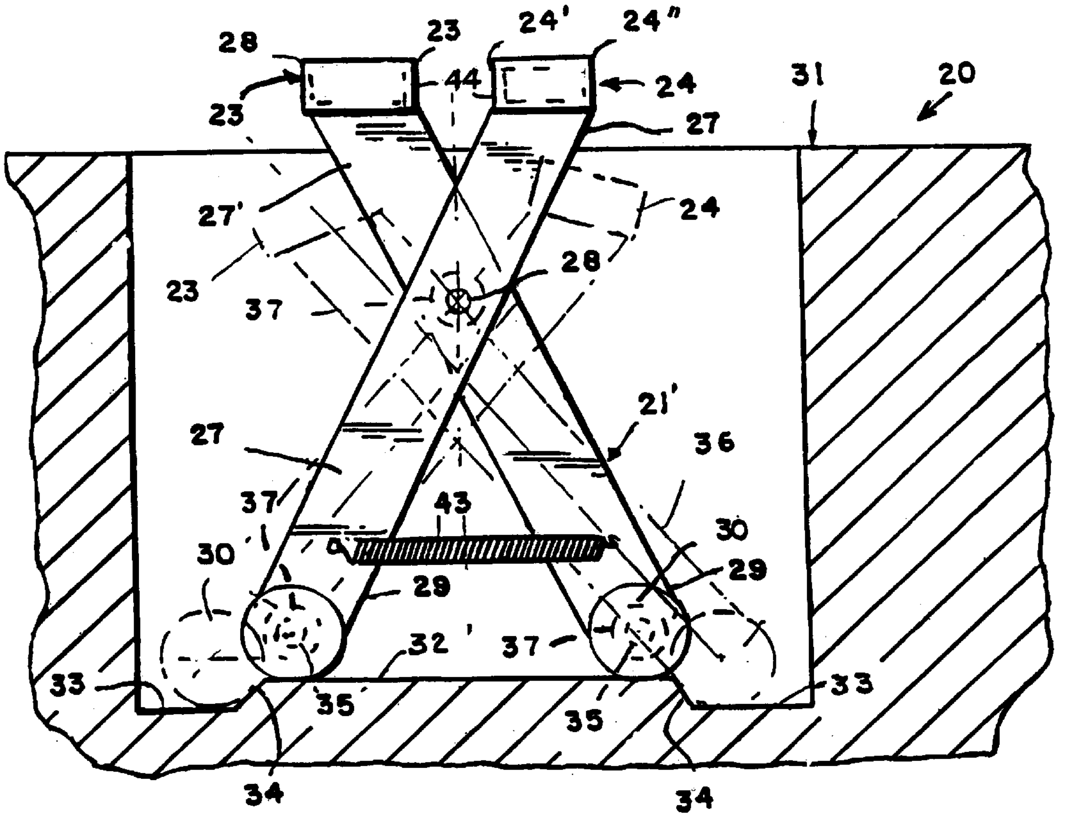
FIG. 5 is an enlarged front cutaway view of the first pair of pivotal acting ridge members shown in solid lines before the downward treatment action of a patient shown in solid lines and with the ridge member shown in phantom lines after their separation pivotal movement.
Figure 6:
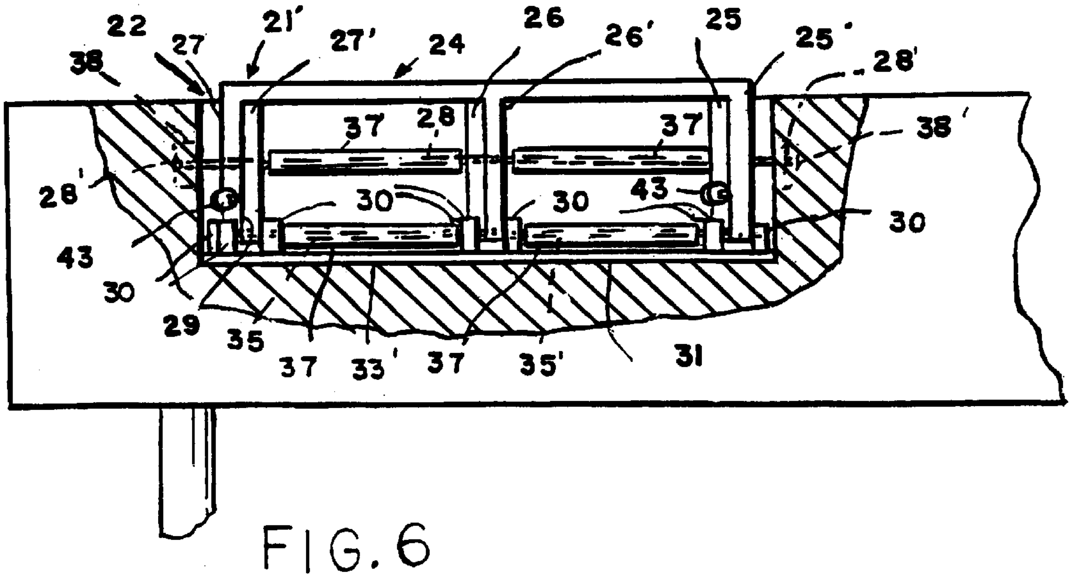
FIG. 6 is an enlarged side elevational view of the first ridge members with portions of the table cutaway to reveal the scissor construction.
Figure 7:
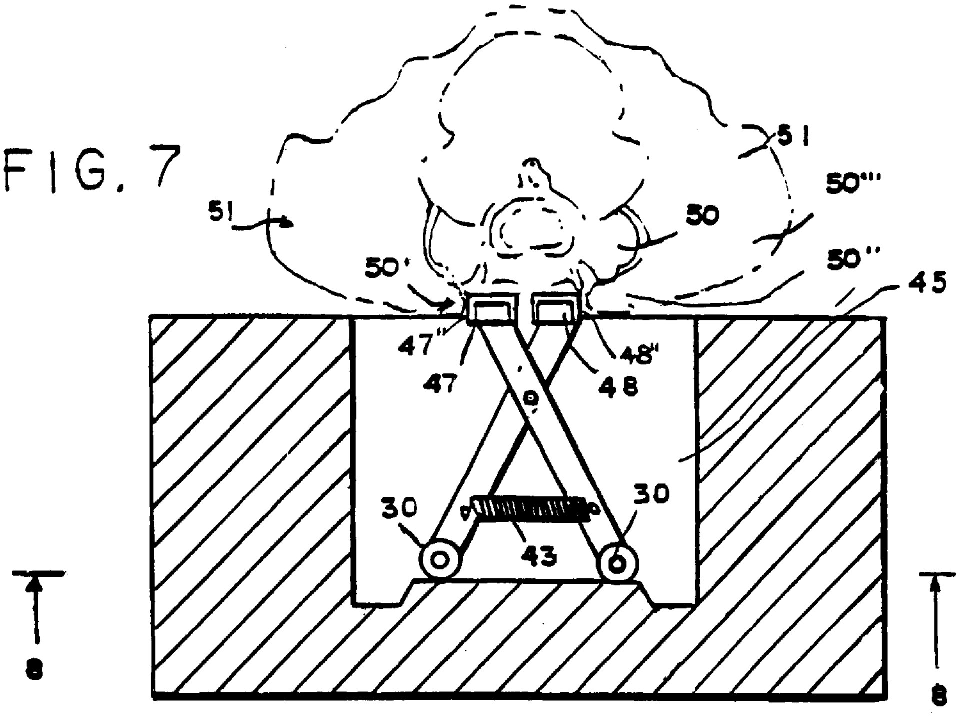
FIG. 7 is a cross sectional end view taken along line 7—7 of FIG. 2.
Figure 8:
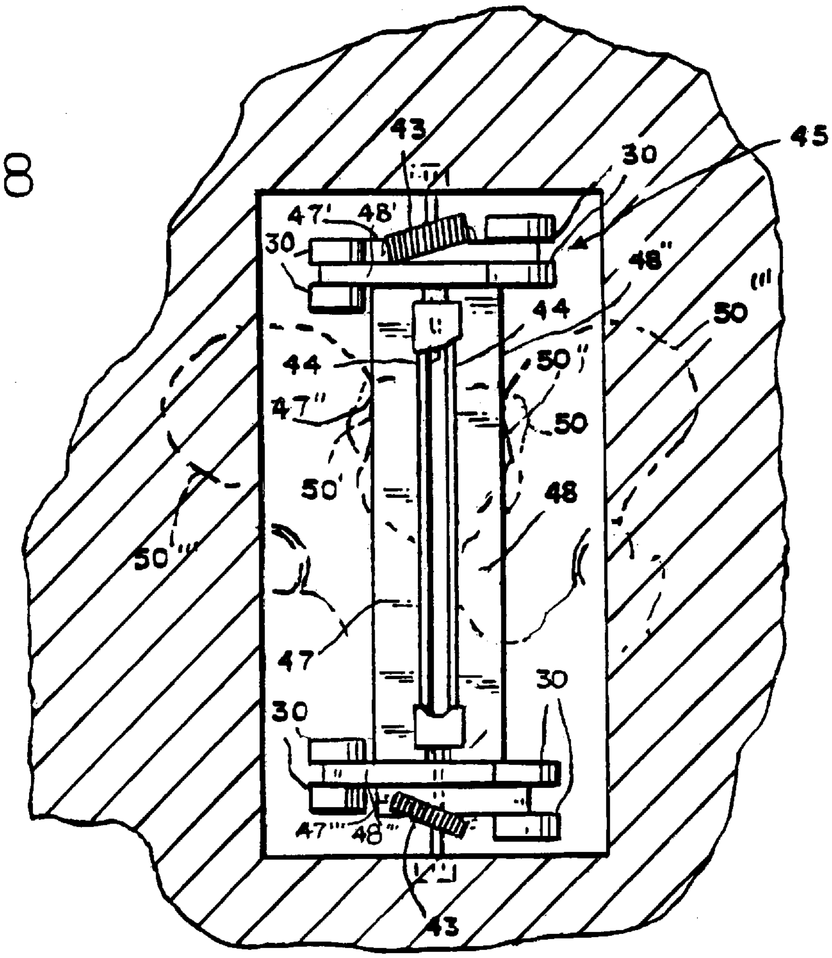
FIG. 8 is a cross sectional inferior or underneath view taken along line 8—8 of FIG. 7.
Figure 9:
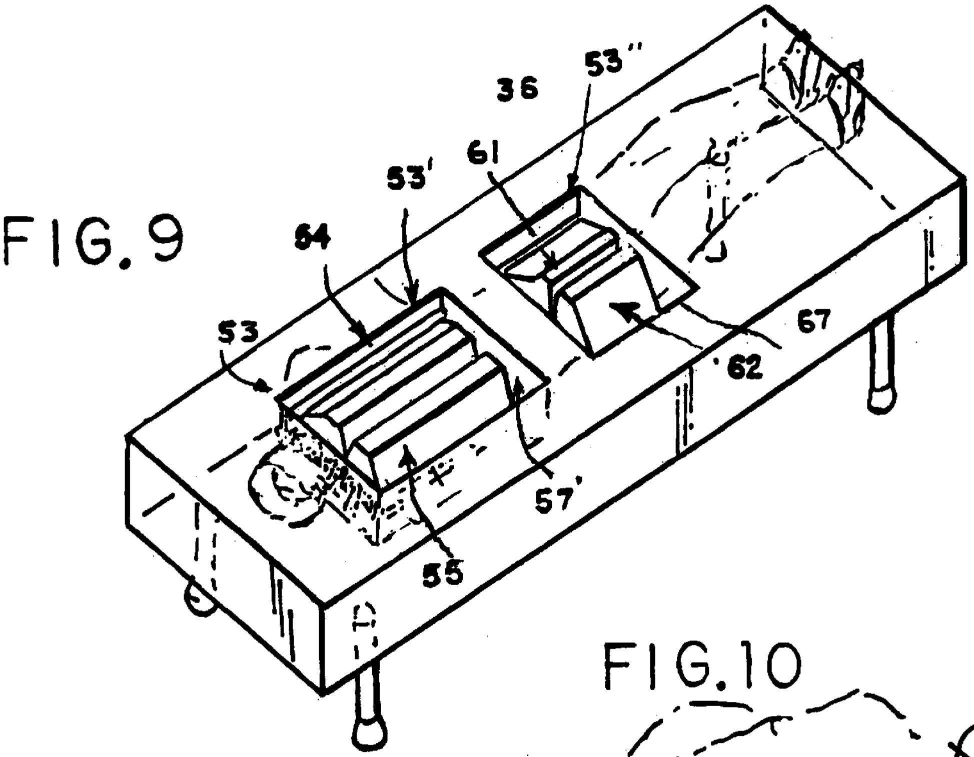
FIG. 9 is a perspective view of the second form of the invention illustrating the table with a pair of slots in the table and a pair of movably mounted mound members mounted in each slot for engaging the back and lower posterior in the spinal column chest portion of a patient and the sacral-iliac joint portion, respectively, of the patient.

The bottom panel 32 in the slot 22 has abrupt drop or step down horizontal surface portions 33 and 33' on opposite side edges 34 and 34' of the bottom panel, which are stepped down from the horizontal surface portion 31, so that the rollers 30 and thereby the scissors and parallel bars or ridges 23 and 24 will drop down suddenly, when the ridges 23 and 24 are pressed down sufficiently causing the ridges 23 and 24 to separate sufficiently to cause the scissors to pivot apart from one another on their common pivot rod 28 from their position shown in solid lines in FIGS. 1–6 to enable their rollers 30 to reach the edges of the upper panel 31, after the parallel ridges 23 and 24 and thereby the scissors have separately or pivoted apart a short distance from one another causing the rollers to roll toward the edges 34 and 34' and drop off the edges onto the lower horizontal surfaces portions 33 and 33', as shown in phantom lines 36 in FIG. 5 due to the pressing down pressure by the treatment operator upon the arms and chest of the patient 36' shows in phantom lines in the drawings. This sudden drop produces a jarring action upon the spinal column of the patient, when lying supine on the table causing realignment of the components of the spinal column, as a beneficial effect.

The spinal treatment apparatus 21' of the upper unit has a pair of bottom common rods 35 and 35', with common rod 35 running through the lower ends of the scissor arms on their one side and the common rod 35' running through the lower ends of the scissor arms on their other side ends, with sleeves 37 on the rods between the scissor arms keeping the scissor arms in spaced uniform alignment with one another as they are pivoted apart and together. Also, the common pivot rod 28 of the scissor arms has spacer sleeves 37 mounted on the rod 28 between each of the three pair of scissors to also keep the scissors in uniform spaced alignment with one another.

A vertical narrow slot 38 is provided in the front wall 39 of the broad slot 22 in the table and a similar vertical slot 38' is provided in the rear wall 40 of the slot 22 in the table, and the common rod 28 has projecting front and rear ends 28' and 28", respectively, which slide in the front and rear slots 38 and 38', respectively, and act to keep the apparatus in alignment in the slot 22 in the table to prevent side to side movement of the rod and apparatus in the slot in the table, while allowing uniform upward and downward pivotal movement of the scissors in the slot 22, guided; by the rod in the slots 38 and 38' in the broad slot 22 in the upper surface of the table.

In this first form of the invention, the upper treatment unit 21' is for primarily treating the thoracic region of the spine by the movement of the parallel bars or ridges 23 and 24, while the lower treatment unit 45 is primarily for treatment of the where the sacrum 50 and ilium 51 joint together to form the sacral iliac joint at the lower end of the spine also referred to as the iliac spine by the movement of the parallel ridges 47 and 48.

In this first form of the invention, the ridges or parallel bars 23 and 24 of the upper unit have cushioning 44 covering along their length. The three pair of scissor members 25,25', 26,26',27,27' each have a spring 43 connected between each pair of scissor members at their lower ends to draw each pair of scissors at their upper and lower ends pivotally toward one another about the pivot rod 28 to thereby draw the pair of ridge members pivotally toward one another in parallel relat. In the first form of the invention, the upper unit for spinal treatment 21', the ridge members 23 and 24 will have their top inner edges 23' and 24' of each of the rectangular elongated ridges made of resilient cushion material 44, as well as their top outer edges 23" and 24". The outer edges 23" and 24" will be spaced approximately 1½ inches apart from one another to allow sufficient space for the spinal column 43 of the patient 36' to be disposed freely between the inner edges of the pair of ridges 23 and 24 without the scissors or ridges 23 and 24 being in direct contact with the spinal column, when the patient is lying supine upon his back upon the table. The front wall 39 of the slot 22 will be adjacent the neck 46 of the patient, while the rear wall 40 of the slot 22 and the third pair of scissors 25 and 25' will terminate approximately adjacent the bottom of the rib cage of the patient.

The second scissor treatment mechanism or lower unit 45 is mounted in a second slot 46 in the table for treatment of sacral iliac problems. It also has a pair of scissor members 47' and 48' mounted at their one ends to the ridge members 47 and 48 and a second pair of scissor members 47"' and 48"' mounted at their one ends to the ridge members 47 and 48 at the other ends of the ridge members, with rollers 30 mounted at the bottom of the scissor members 47',48",47"', 48" A common rod 28 also extends through the pair of scissor members to provide the pivotal connections for the scissor members 47' and 48' relative to one another and the scissor members 47"' and 48"' relative to one another. The ridge members and scissor members are pivotally mounted on the rod for pivotal movement apart for treatment of the sacral-iliac repositioning and problems associate with it. The common rod 28 of the second unit 45 is also mounted in vertical front and rear slots 38 and 38' which function similar to slots 38 and 38' of the upper unit to keep the ridge members 47 and 48 is vertical alignment in the slot 46 when the ridge members are pivoted apart and toward one another in the slots.

The structure of the second scissor treatment mechanism or lower unit 45 is similar to the structure of the first spinal treatment mechanism or upper unit 21', only that the second treatment mechanism is intended to be shorter than the first mechanism 21', with the first mechanism 21' intended to be approximately 18 inches long while the second scissor mechanism 45 is intended to be approximately 12 inches long.

The second sacral-iliac treatment mechanism or lower unit 45 is mounted in the table 21 below or spaced along the table from the spinal treatment mechanism or upper unit 21'. The second treatment mechanism is for treating sacral-iliac problems at the lower end of the spine and has the pair of ridges 47' and 48' for contact with the bottom ot the patient's body directly beneath the sacrum 50 of the patient when the patient is lying supine upon the table upon his back and serve to support the sacrum and are adjacent the left and right sides medial surfaces 50' and 50" of the posterior superior iliac spine which form the sacral-iliac joints of the hip bones of the body. The dual pair of scissor arms 47' and 48' and 47" and 48" are pivotally mounted together at the common rod 28 to pivot apart from one another in a manner similar to the upper spinal treatment mechanism 21' with a similar springs 43' connecting each pair of scissor arms together and urging them toward one another similar to the upper unit.

The ridge members 47 and 48 pivot apart in a manner similar to the upper spinal treatment mechanism 21', so that frontal pressure when applied upon the lower portion of the patient while lying supine upon the table with his lower posterior upon the ridges 47 and 48, as described, the reactive force upon the ridges will cause them to separate in a pivotal action and the ridges 47 and 48, when pivoted apart, provide bilateral parallel leverage contact in separate opposite directions against the confronting portions 50' and 50" of the sacral medial posterior superior iliac spine 50"' to force the iliac apart outward laterally of the pelvic unit, or sacrum. In the sacral iliac mechanisms, ridge members 47 and 48 will be spaced approximately 3 inches apart from one another so the spacing is slightly larger than the spinal mechanism spacing of the upper unit. The sacrum 50 rests primarily upon the top faces of the ridges 47 and 48 with the outer edges 47" and 48" in significant contact with the posterior superior iliac spine, so that the downward force of the operator upon the top of the lower portion of the body causes a downward impact upon the ridges 47 and 48 triggering them apart and thereby producing an outward compounded bilateral directional force upon the spine portions 50' and 50" of the spine at the iliac joints, forcing or jarring the posterior iliac superior spine apart.

Operation of the Upper unit Spinal Treatment Mechanism of the First Form the Invention In the first form of the invention, for treatment of the upper spine with the spinal treatment mechanism 21', the patient will be placed on the table on his back with his back resting on the ridges 23 and 24 and his arms 36" and 36"' crossed in a position as generally approxmately shown in FIGS. 1–5, inclusive, so that the front or top wall 38 of the slot 22 will be adjacent the neck of the patient as shown in phantom lines in the Figures. The space between the top inner edoes 23' and 24' of the ridges 23 and 24, as shown in solid lines before the ridges are separated from one another by the pressing action, will be approximately 1½ inches apart as previously indicated to allow space for the spinal column 43 there between and is slightly larger than the spinal column width to allow the spinal column to be between the ridges 23 and 24 with the rib transverse area of the spinal column resting on the ridges. Also, the rear wall 38' of the slot 22 and the rear ridges or ends of the ridges will terminate approximately at the back of the patient at the bottom of the rib cage of the patient upon the table, since in both forms of the invention, as well as the mounds 49 and 49' of the upper unit 53' in the second form of the invention will rest upon the back of the rib cage of the patient, as shown in FIGS. 1–7 and 9–13, respectively.

The spinal treatment operator will, when the patient is in the position as just described in connection with the upper unit of the first form press down upon the crossed arms 36" and 36"' of the patient; which will cause the ridge members to press against the back of the patient on each side of the spinal column; and with continuing downwards pressure in opposition to the springs acting as a spring return, will cause the ridge members to pivot apart on the pivot rod 28 with the rollers 30 rolling from their position shown in solid lines to the edges of the upper horizontal portion 31 and then drop suddenly off the edges onto the lower horizontal surfaces 33 and 33" . This separation movement of the ridges upon the back, ending in a sudden downward impact action upon the back when the rollers drop off the edges onto the lower horizontal surfaces tends to act or cause a compound bilateral directional force to the spine 43 to be jarred back into alignment with the curvature of the rib heads 44', while the rib heads on the one side are tending to separate momentarily from the rib heads on the other side under the separation movement of the ridge members 23 and 24 from one another during the initial downward pressure of the treatment operator upon the patient as just described.

The springs 43' connected between the scissor arms 25, 26, and 27, and arms 25', 26', and 27' respectively act to draw the respective arms and thereby the ridge members 23 and 24 toward one another and thereby return the scissor arms close together and the ridge member 23 and 24 close together upon the operator's removal of the downward pressure upon the arms and chest of the Operation of the sacral-iliac scissor mechanism 45 is similar to the upper spinal treatment mechanism 21'. The patient is placed supine on the table with the sacrum 50 of the patient's body resting upon the parallel ridges 47 and 48, between confronting portions of the sacral posterior iliac spine. The treatment operator has the patient's knees crossed and places his right hand one the patient's right knee and left hand upon the patient's left knee and thrusts downward toward the patient's dorsal posterior of his body while the patient is on his back on the table. Applying this downward mechanical force upon the patient's knees causes the ridges 47 and 48 to separate in their bilateral scissor like action with their rollers 30 dropping off the ledges in the slot, similar to the ledge and operation of the upper spinal treatment mechanism. This lateral scissors action for each sacral-iliac joint with the separation travel ending in the rollers dropping off their ledges produces a disposition articulation action upon the sacral iliac articulation joint structure separating the hip joint from the sacral iliac momentarily to free the structures from one another. The separation of the ridge members 47 and 48 will be approximately 3 inches in contrast to the separation of the ridge members 23 and 24 in the upper spinal treatment mechanism of approximately 1½ inches.

Second Form of the Invention

Figure 10:
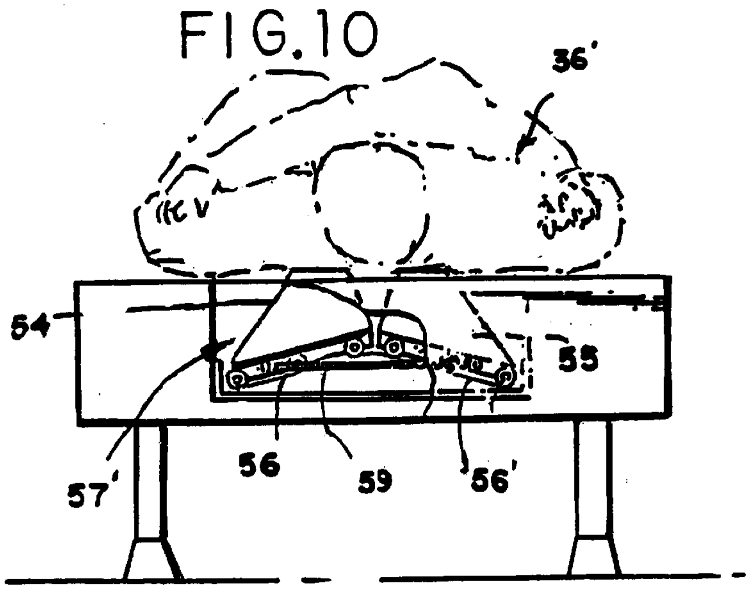
FIG. 10 is a front elevational end view of the second form of the invention.
Figure 11:
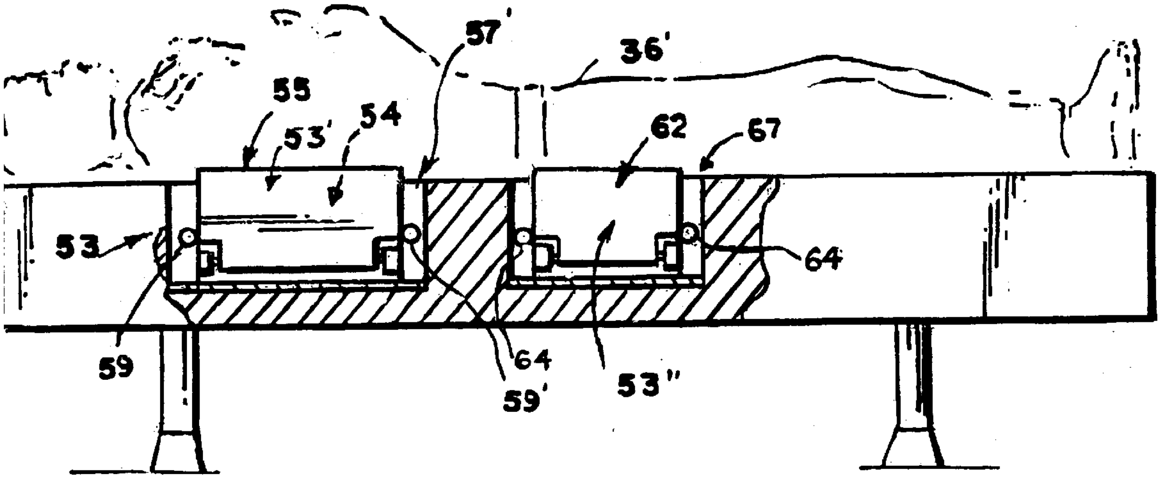
FIG. 11 is a side elevational view of the second alternate form of the treatment table a cutaway of the table showing the dual slots with the dual pair of movable ridge members in each slot, movable in a straight line action.
Figure 12:
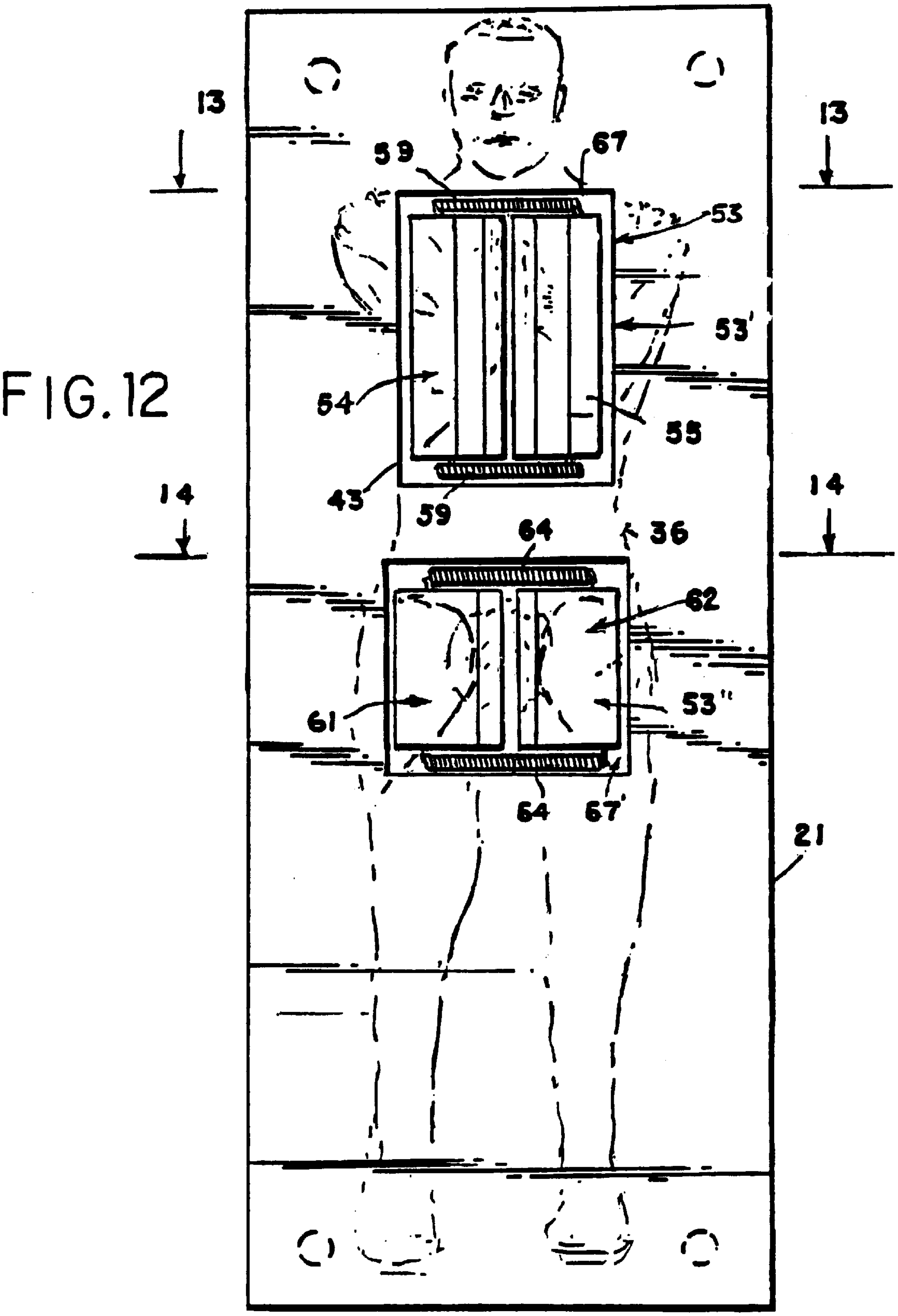
FIG. 12 is a top plan view of the second alternate form of chiropractic treatment table.

A second form 53 of the invention is illustrated in FIGS. 9–15 and it has an upper spinal treatment mechanism 53' and a lower sacral iliac treatment mechanism 53" . In the second form of the invention, the upper spinal treatment mechanism 53' has a pair of ridge or mound members 54 and 55 in the slot 57' and the mound members are movably mounted on opposing inclined surfaces 56 and 56' in the upper slot 57' of the table. The opposing inclined surfaces incline laterally downward and away from one another in a the slot in a straight line laterally opposed travel path in relation to one another and in relation to the length of the table. Each mound member has rollers 58 mounted in each of their four corners to rotatably support the ridge or mound members on the inclined surfaces, with the inclination causing the ridge member under gravity to move downward and away from one another in a straight line action as shown by the arrows in FIG. 10. The mounds are spring urged together by a pair of springs 59 and 59' connecting the mounds 54 and 55 together at each end and are of sufficient strength to overcome the gravitation weight of the mounds or ridges 54 and 55 and urge the ridge members upward toward and against one another as shown in FIG. 10. The patient, shown in phantom lines, is lying supine on the table 21 on his back 29 with the ridge members 54 and 55 of the upper unit 53' engaging his back on each side of his spinal column 43. The spring members 59 and 59' have their outer ends connected to the ridge members 54 and 55 at opposite ends on posts 59" fixed to respective ridge members 54 and 55.

In the second form of the invention, the lower sacral-iliac parallel ridge mechanism 53" has a structure and operation similar to the parallel ridge mechanism 53' of the upper spinal treatment, having a second pair of mounds 61 and 62 mounted on rollers 63 in the second slot 67 of the table. The mounds 61 and 62 are also spring urged together by springs 64 connected the mounds together at their ends with the mounds also positioned on opposed downwards inclined surfaces 66 and 66' to allow the mounds to travel apart and downward on the incline while the springs urge the mounds back upward toward one another. This is essentially the same operation as the upper mechanism 53' for the upper spinal treatment and the main difference between the two is that the upper spinal treatment mechanism 53' is longer, approximately 18 inches, than the lower sacral-iliac mechanism 53" . The lower sacral-iliac treatment mechanism 53" is mounted in a second slot 67' in the table 21, below the first slot 67.

Operation of Second Form of the Invention

The operation of the second form of upper and lower spinal treatment mechanism is similar to the first form, only that the separation movement is in a straight line action rather than a pivotal action.

The treatment table 20, in both forms, will be used to correct misalignment of upper spinal and lower sacral-iliac components. The patient may ly upon the table on his back with his back upon the upper movable mounds 54 and 55 for treatment of the upper spine, for example, with the spinous of the spine 43 has move out of alignment with the curved portion 44" of the head 44' of the rib, such as generally shown in FIGS. 9–13, inclusive.

Figure 13:
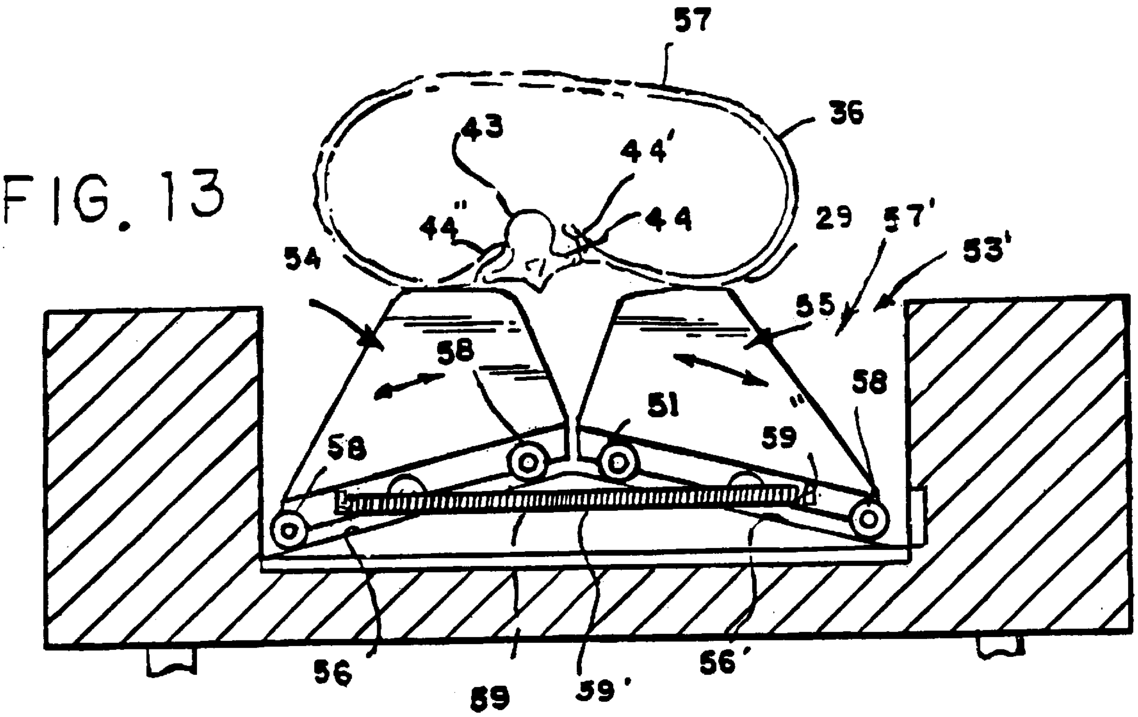
FIG. 13 is a end view taken along line 13—13 of FIG. 12.
Figure 14:
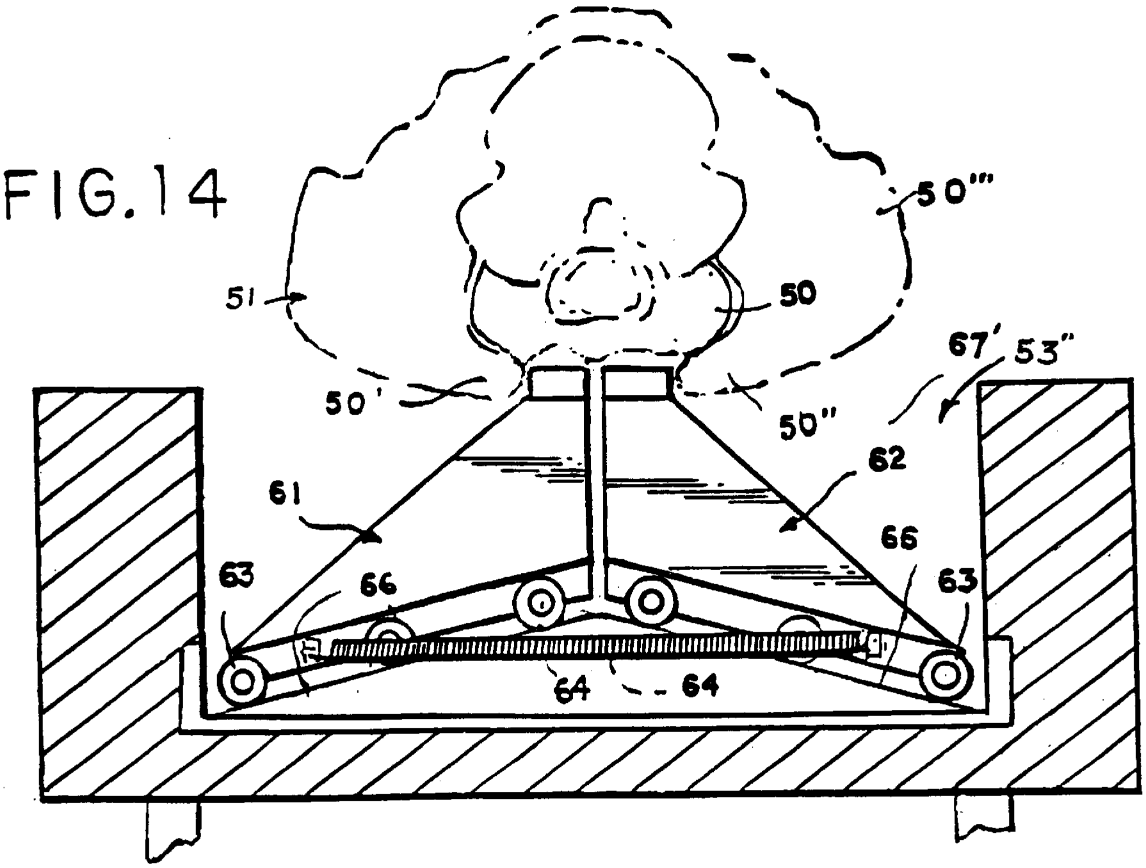
FIG. 14 is a end view taken along line 14—14 of FIG. 12.
Figure 15:
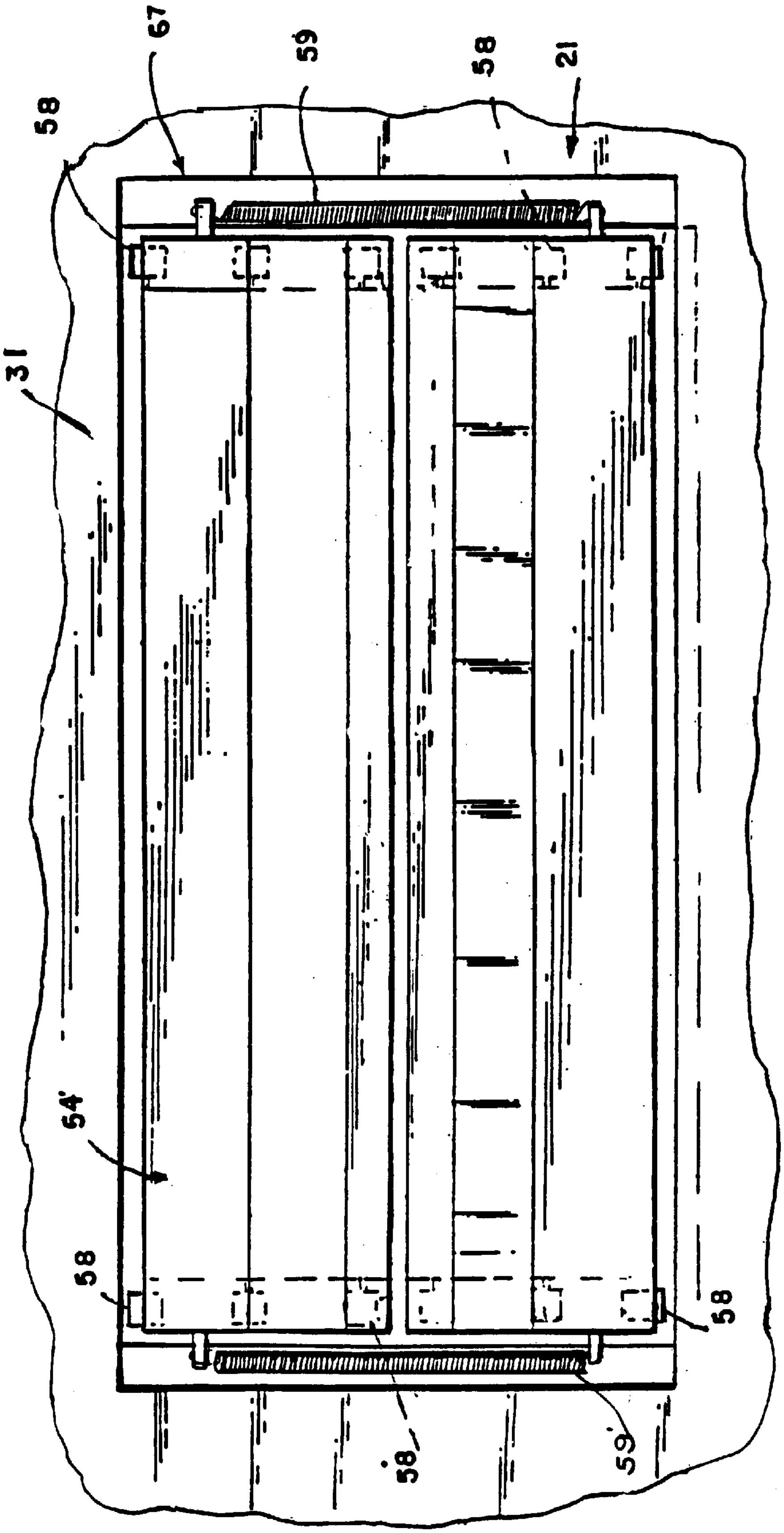
FIG. 15 is a top view of the second form of spinal ridge mechanism.

The upper movable ridges 54 and 55 of the treatment table, by moving bilaterally away from one another, will cause the rib heads on each side of the rib cage 68 to move away from the spinous 44, for example, so that the rib head can slip back into position with the cup portion 44' of the rib head about the spinous on the transverse side of the spine, so a correct aligned position is attained similar in mirror image to the spinous position on the left side of the spine as shown generally in FIG. 13. In both forms of the invention it is intended that the ridges 23 and 24 and 54 and 55 will rest on the back of the rib cage of the patient, when the treatment operator presses down on the crossed arms and chest of the patient for the treatment as already described.

In the second form of the invention the upper and lower mechanism 53' and 53" have side walls 70 and 70' in their respective slots 57 and 67' provide an abrupt stop to the mounds or ridges of the upper and lower mechanisms when the treatment operator presses down on the arms and chest of the patient in the upper mechanism or lower frontal portions of the patient triggering the bars in the upper or lower unit to separate, when the rollers 58 engage the side walls. In contrast, in the first form of the invention, the step down ledges on each side edge of the horizontal surface in the slots, the supporting rollers of the scissors provide an abrupt drop and then the side walls 60 and 60' of the slots provide an abrupt stop to the rollers of the scissors of the apparatus. This abrupt drop in effect transmits in a compounded bilateral directional impact action to the spinal column of the patient to cause components of the spine, out of alignment, be forced back into alignment. The abrupt stop of both forms of the invention, upper and lower units, the ridge members 23,24, 47,48, 54, 55, 61 and 62 will project at least approximately 1 inch above the adjacent top surface 31 of the table surrounding the slots in the table, when the ridge members are at their closest position to one another, as shown in the drawings. When the ridge members have separated in their path downward and away from one another, the ridge members will still project slightly above the top surface of the table, when the ridge members reach the end of their downward and outward movement and have engaged the sudden stops in the slots. The ridge members of the upper units in both forms of the invention project above the top surface of the table at all times, so that they can adequately engage the back of the patient on each side of the spine at all times to enable the downward pressure on the chest to cause a reactive upward pressure on the back sufficient to cause a sufficient separation and realignment effect upon the spinal components. The springs in both forms of the invention will have sufficient strength to urge the ridge members back toward one another into engagement with one another as illustrated in the drawings, after any lateral travel is completed by frontal downward pressure upon frontal portions of the patient's body and the pressure force has been removed or stopped, with the springs causing the ridge member to roll or pivot back upward to one another for the next spinal treatment usage. The weight of the patient's body alone resting upon the ridge members will not be sufficient to overcome the force of the springs and cause the ridge members to separate, as additional frontal pressure upon the patient's body, by the treatment operator applying pressure to the frontal portion of the patient's body by some means, is necessary to overcome the strength of the springs and cause the ridge members to separate from one another from their position shown in the drawings.

It will be obvious that various changes and departures may be made to the invention without departing from the spirit and scope thereof, and accordingly, it is not intended that the invention be limited to that specifically described in the specification or as illustrated in the drawings, but only as set forth in the appended claims wherein:

What is claimed is:

1. A chiropractic table device comprising a elongated table member, said table member having a slot in its top surface and adapted to receive a patient supine on his back longitudinally on the table upon the top surface, a back treatment apparatus mounted in said slot of said table, said apparatus comprising a pair of ridge members laterally parallel to one another with said ridge members being movable laterally of the length of said table toward and away from one another, spring means urging said ridge members laterally toward one another, said ridge members being adapted to project upward in the slot in the top surface of the table to engage the back of a patient when the patient is lying supine on the table, with said ridge members on opposite sides of the spinal column of the patient, wherein a treatment operator may press down on the chest of the patient and cause the ridge members to slide laterally apart from one another with the ridge members acting to engage the back of the patient when the downward pressure is applied with the lateral sliding parallel sliding apart of the ridge members acting to cooperate with the spine of the patient to remove any misalignment of the spine of the patient or the tissue adjacent to the spine, and with the spring means urging the ridge members back toward one another after the downward pressure.

2. A spinal treatment table comprising an elongated table member having a slot in its top surface, a ridge treatment apparatus mounted in said slot having a pair of separable ridge members with upper surfaces of the ridge members projecting above the top surface of the table and lower surfaces of the ridge members contacting a bottom surface of said slot, said ridge members being adapted to engage the back of a patient lying supine upon the top surface of the table with the ridge members engaging the back on opposite sides of the spinal column, said ridge members being laterally separable, under downward pressure force upon the chest of the patient, in a laterally opposing movement relative to the table, means on said bottom surface of said slot for providing an abrupt stop to the ridge members at the end of the separation movement, with the lateral movement tending to provide a separation space for spinal components of the patient out of alignment to allow them back into component alignment, with the abrupt stop at the end of the separation movement acting to jar the components back into alignment upon their separation due to the ridge movement.

3. A spinal treatment table according to claim 2, wherein said ridge treatment apparatus includes a step down ledge means at the bottom surface of said slot, said stop means being at the bottom of said step down ledge means enabling the ridge members to drop down abruptly upon reaching the end of its lateral outward movement and then stop abruptly at a bottom of the step down ledge means.

4. A treatment table for treatment of joints of the bone structure of a person comprising a horizontal table, said table having a first slot in the top surface of the table with the top surface of the table adapted to receive a patient lying supine on his back on the table, a pair of separable ridge members mounted in said slot and having their upper surface slightly above the adjacent top surfaces of the table for engagement with portions of the patient's body, said ridge members being movable laterally apart from one another in response to downward pressure upon the front of the patient for engagement of the ridges with portions of the patient's body and with said separation of said ridges acting to articulate selected joints of the patient's body to correct misalignment of the joints.

5. A treatment table according to claim 4, wherein said table has a second slot in alignment within said first slot in the top surface of the table, a second pair of ridge members movably mounted for separation movement from one another, with said first pair of ridge members in said first slot being adapted to be aligned with the patient's back with one ridge member on one side of the patent's spinal column and the other ridge member aligned on the other side of the spinal column in the area generally between the neck and bottom of the lungs of the patient with the separation movement of the ridge members of the first slot beina adapted for articulation treatment of the spinal column of the patient said second pair of ridge members being adapted to be aligned with the sacral-iliac joints at the posterior of the patient when lying supine on his back on the table, with the second pair of ridge members being adapted to move apart in response to downward pressure upon the front of the patient for articulation treatment of the sacral iliac of the patient.

* * * * *